United States Patent
Shibata et al.

(10) Patent No.: US 12,222,368 B2
(45) Date of Patent: Feb. 11, 2025

(54) LIQUID ANALYSIS DEVICE AND SENSOR UNIT

(71) Applicant: HORIBA Advanced Techno, Co., Ltd., Kyoto (JP)

(72) Inventors: Manabu Shibata, Kyoto (JP); Yuichiro Komatsu, Kyoto (JP); Hiroki Minowa, Kyoto (JP)

(73) Assignee: HORIBA ADVANCED TECHNO, CO., LTD., Kyoto (JP)

( * ) Notice: Subject to any disclaimer, the term of this patent is extended or adjusted under 35 U.S.C. 154(b) by 294 days.

(21) Appl. No.: 17/595,431

(22) PCT Filed: May 15, 2020

(86) PCT No.: PCT/JP2020/019537
§ 371 (c)(1),
(2) Date: Nov. 16, 2021

(87) PCT Pub. No.: WO2020/250622
PCT Pub. Date: Dec. 17, 2020

(65) Prior Publication Data
US 2022/0196703 A1 Jun. 23, 2022

(30) Foreign Application Priority Data
Jun. 10, 2019 (JP) ................. 2019-108265

(51) Int. Cl.
*G01N 33/18* (2006.01)
*G01R 1/067* (2006.01)
*H03M 1/12* (2006.01)

(52) U.S. Cl.
CPC ............. *G01R 1/067* (2013.01); *G01N 33/18* (2013.01); *H03M 1/12* (2013.01)

(58) Field of Classification Search
CPC ........ G01R 1/067; G01N 33/18; G01N 33/00; G01N 33/20; G01N 33/22; G01N 29/24; H03M 1/12
See application file for complete search history.

(56) References Cited

U.S. PATENT DOCUMENTS 6,487,912 B1 * 12/2002 Behm ..................... G01D 1/00
73/753
2005/0103134 A1   5/2005 Brundage
(Continued)

FOREIGN PATENT DOCUMENTS

| CN | 103542875 A | 1/2014 |
| CN | 206208882 U | 5/2017 |

(Continued)

OTHER PUBLICATIONS

European Patent Office, Extended European Search Report Issued in Application No. 20821722.4, Dec. 7, 2022, Germany, 9 pages.
(Continued)

*Primary Examiner* — Suman K Nath
(74) *Attorney, Agent, or Firm* — Alleman Hall & Tuttle LLP (57) ABSTRACT

The present invention reduces a running cost in a liquid analysis device and reduces electromagnetic noise superimposed on an analog signal. The present invention includes a sensor portion configured to contact a liquid and output an analog signal corresponding to a predetermined measurement target item, a conversion portion configured to convert the analog signal obtained by the sensor portion into a digital signal, and a device body to which the conversion portion is connected by a wire or wirelessly, the device body being configured to acquire the digital signal from the conversion portion. The sensor portion and the conversion portion are attachable to and detachable from each other, the sensor portion includes a connection plug that electrically connects (Continued)

to the conversion portion, and a metal shield is provided at a connection portion between the connection plug and a wire of the sensor portion.

11 Claims, 10 Drawing Sheets

(56) References Cited

U.S. PATENT DOCUMENTS

| | | | |
|---|---|---|---|
| 2010/0248283 A1* | 9/2010 | Xiao | G01N 21/553 |
| | | | 435/29 |
| 2011/0020919 A1* | 1/2011 | Fulton | B01L 3/0275 |
| | | | 422/69 |
| 2011/0204876 A1 | 8/2011 | Mieth et al. | |
| 2014/0012530 A1 | 1/2014 | Reinhold et al. | |
| 2015/0300981 A1 | 10/2015 | Arquint et al. | |
| 2016/0139101 A1 | 5/2016 | Scott et al. | |
| 2016/0354786 A1 | 12/2016 | Thei et al. | |

FOREIGN PATENT DOCUMENTS

| | | |
|---|---|---|
| CN | 207456517 U | 6/2018 |
| CN | 108571996 A | 9/2018 |
| CN | 212622539 U | 2/2021 |
| GB | 2196202 A | 4/1988 |
| JP | S5246892 A | 4/1977 |
| JP | S5363889 U | 5/1978 |
| JP | S58103658 A | 6/1983 |
| JP | H04127566 U | 11/1992 |
| JP | H11153594 A | 6/1999 |
| JP | 2004286685 A | 10/2004 |
| JP | 2005077252 A | 3/2005 |
| JP | 2005114697 A | 4/2005 |
| JP | 2010151729 A | 7/2010 |
| JP | 2013142964 A | 7/2013 |
| JP | 2019020246 A | 2/2019 |
| WO | 2018112012 A1 | 6/2018 |

OTHER PUBLICATIONS

ISA Japan Patent Office, International Search Report Issued in Application No. PCT/JP2020/019537, Jul. 21, 2020, WIPO, 5 pages.
China National Intellectual Property Administration, Office Action Issued in Application No. 202010472868.7, Jun. 24, 2024, 26 pages.
China National Intellectual Property Administration, Office Action and Search Report Issued in Application No. 202010472868.7, Dec. 9, 2024, 27 pages.

* cited by examiner

EXAMPLE OF SCREEN DISPLAY

FIG. 5(C)

WHEN pH SENSOR,
EC SENSOR, AND DO SENSOR
ARE CONNECTED

FIG. 5(B)

WHEN pH SENSOR AND
EC SENSOR ARE
CONNECTED

FIG. 5(A)

WHEN pH SENSOR IS
CONNECTED

FIG. 6

OPERATION BUTTON GROUP

WITH CABLE WOUND AROUND

FIG. 10(A)

IN USE

LIQUID ANALYSIS DEVICE AND SENSOR UNIT

TECHNICAL FIELD

The present invention relates to a liquid analysis device that analyzes a liquid and a sensor unit that analyzes a liquid.

BACKGROUND ART

For example, as a device that measures pH, dissolved oxygen, and the like in a liquid such as environmental water, industrial water, or water in sewage treatment, there is a device including a sensor unit that is immersed in a liquid and outputs a detection signal corresponding to a predetermined measurement target item, and a device body that acquires the detection signal from the sensor unit and displays a measurement value, as disclosed in Patent Literature 1.

Here, the sensor unit includes a sensor portion that outputs an analog signal corresponding to the measurement target item, a conversion portion that amplifies the analog signal from the sensor portion and converts the analog signal into a digital signal, and a container that accommodates the sensor portion and the conversion portion.

However, in the sensor unit, the container cannot be separated into a portion accommodating the sensor portion and a portion accommodating the conversion portion of A/D. Therefore, in a case where the sensor portion is replaced due to deterioration of the sensor portion or the like, it is necessary to also replace the conversion portion that is not originally required to be replaced, and thus a running cost increases.

CITATION LIST

Patent Literature

Patent Literature 1: JP 2019-20246 A

SUMMARY OF INVENTION

Technical Problem

Here, the inventors consider that a sensor portion that is immersed in a liquid and outputs an analog signal corresponding to a predetermined measurement target item, and a conversion portion that converts the analog signal obtained by the sensor portion into a digital signal are attachable to and detachable from each other. It is conceivable that the sensor portion has a connection plug that electrically connects to the conversion portion. In this case, there is a possibility that electromagnetic noise is applied to the analog signal from a connection portion between the connection plug and a wire of the sensor portion.

Therefore, the present invention has been made to solve the above problem, and a main object of the present invention is to reduce a running cost in a liquid analysis device and reduce electromagnetic noise superimposed on an analog signal.

Solution to Problem

A liquid analysis device of the present invention includes a sensor portion configured to be immersed in a liquid and output an analog signal corresponding to a predetermined measurement target item, a conversion portion configured to convert the analog signal obtained by the sensor portion into a digital signal, and a device body to which the conversion portion is connected by a wire or wirelessly, the device body being configured to acquire the digital signal from the conversion portion, in which the sensor portion and the conversion portion are attachable to and detachable from each other, the sensor portion includes a connection plug that electrically connects to the conversion portion, and a metal shield is provided at a connection portion between the connection plug and a wire of the sensor portion.

In this liquid analysis device, since the sensor portion and the conversion portion are attachable to and detachable from each other, when the sensor portion is replaced, it is sufficient to replace only the sensor portion and not necessary to replace the conversion portion. Thus, a running cost of the liquid analysis device can be reduced. Then, the metal shield is provided at the connection portion between the connection plug and the wire of the sensor portion, the electromagnetic noise superimposed on the analog signal from the connection portion between the connection plug and the wire of the sensor portion can be reduced, and measurement accuracy can be improved.

In a case where the sensor portion and the conversion portion are integrated in a state of being electrically connected by the connection plug, and are operated by being held in a hand, electromagnetic noise is likely to be added due to static electricity from the hand. In this case, effects of the present invention become more remarkable.

As the sensor portion, a sensor capable of detecting a value indicating properties of a liquid, such as a pH sensor, a dissolved oxygen sensor, a conductivity sensor, an oxidation-reduction potential sensor, an ion concentration sensor for calcium, potassium, or the like, or a turbidity sensor, can be considered. In these cases, the pH sensor is particularly susceptible to electromagnetic noise, and an SN ratio deteriorates. It is therefore desirable that the metal shield is provided in a sensor portion that measures pH as a measurement target item.

Whether the output of the sensor portion is stable during measurement or calibration is confirmed. Here, although a display of the device body indicates that the output of the sensor portion is stable, a user is often more aware of the sensor unit including the sensor portion and the conversion portion, and it cannot be said that the liquid analysis device is usable. Therefore, in order to improve the usability of the liquid analysis device, the conversion portion desirably includes a notifier that provides notification that the output of the sensor portion is stable during measurement and calibration.

The device body can acquire measurement results of a plurality of measurement points or a plurality of measurement target items by connecting a plurality of the conversion portions to which each of the sensor portions is attached. At this time, in order to facilitate handling of the plurality of sensor units including the sensor portion and the conversion portion, it is desirable to include a coupling mechanism that couples the plurality of conversion portions to each other. Thus, the user can easily hold the plurality of sensor units with one hand.

The coupling mechanism desirably couples the plurality of conversion portions for at least one of a position from a bottom of water to a sensing portion (for example, a response glass in a glass electrode) or a position from a water surface to the sensing portion in each of the sensor portions attached to each of the plurality of conversion portions to be an identical position. This configuration facilitates installation of the plurality of sensor portions, for example, at an identical depth position.

The plurality of measurement target items can be measured at once as long as the plurality of conversion portions to which the plurality of sensor portions for different measurement target items are attached are connected to the device body. In this configuration, the device body desirably includes a calibrator that simultaneously calibrates the plurality of sensor portions for different measurement target items. Here, the simultaneous calibration means that the calibration of a plurality of sensors is started at the same timing, and calibration processing for each sensor after the start of the calibration is performed in parallel. In this configuration, calibration of each sensor portion can be performed at once, and calibration time can be shortened. At this time, it is conceivable that the device body calibrates the plurality of sensor portions for different measurement target items by using different types of calibration substances.

The device body desirably includes a connection port to which a cable extending from the conversion portion is connected, and a sensor recognizer that recognizes the sensor portion attached to the conversion portion connected to the connection port. This configuration achieves connection to a common connection port regardless of the type of the sensor portions attached to the conversion portions.

When it is considered that liquid analysis is performed not only in a state where the device body is held in a hand but also in a state where the device body is placed, it is conceivable that the device body is provided with a stand member that supports the device body in an inclined state or a standing state. In this configuration, the cable connecting the conversion portion and the device body is desirably configured to be wound around the stand member. This configuration allows the cable to be gathered and to be less likely to interfere when the liquid analysis device is carried or stored.

A sensor unit of the present invention includes a sensor portion configured to contact a liquid and output an analog signal corresponding to a predetermined measurement target item, and a conversion portion configured to convert the analog signal obtained by the sensor portion into a digital signal and output the digital signal to outside, in which the sensor portion and the conversion portion are attachable to and detachable from each other, the sensor portion includes a connection plug that electrically connects to the conversion portion, and a metal shield is provided at a connection portion between the connection plug and a wire of the sensor portion.

Advantageous Effects of Invention

In the present invention described above, since the sensor portion and the conversion portion are attachable to and detachable from each other, when the sensor portion is replaced, it is sufficient to replace only the sensor portion and not necessary to replace the conversion portion. Thus, a running cost of the liquid analysis device can be reduced.

LIST OF REFERENCE CHARACTERS

100 liquid analysis device
2 sensor unit
sensor portion
conversion portion
3 device body
P1 to P3 connection port
3e calibrator
3c sensor recognizer
212 connection plug
5 metal shield
6 coupling mechanism
7 notifier
8 stand member

DESCRIPTION OF EMBODIMENT

Hereinafter, a liquid analysis device according to an embodiment of the present invention will be described with reference to the drawings.

1. Device Configuration

A liquid analysis device 100 according to the embodiment measures predetermined measurement target items of a liquid to be measured, such as environmental water such as rivers, lakes, and oceans, industrial water, and water during sewage treatment.

Here, examples of the measurement target items include a value indicating a property of a liquid including at least one of pH, conductivity (EC), dissolved oxygen (DO), oxidation-reduction potential (ORP), an ion concentration of calcium, potassium, or the like, turbidity, a number of cells of chlorophyll, cyanobacteria, or the like, a nitric acid concentration, or an ammonium concentration, a water depth, a water level, and the like. Hereinafter, the liquid analysis device 100 capable of measuring three measurement target items of pH, conductivity (EC), and dissolved oxygen (DO) will be described.

Figure 1:
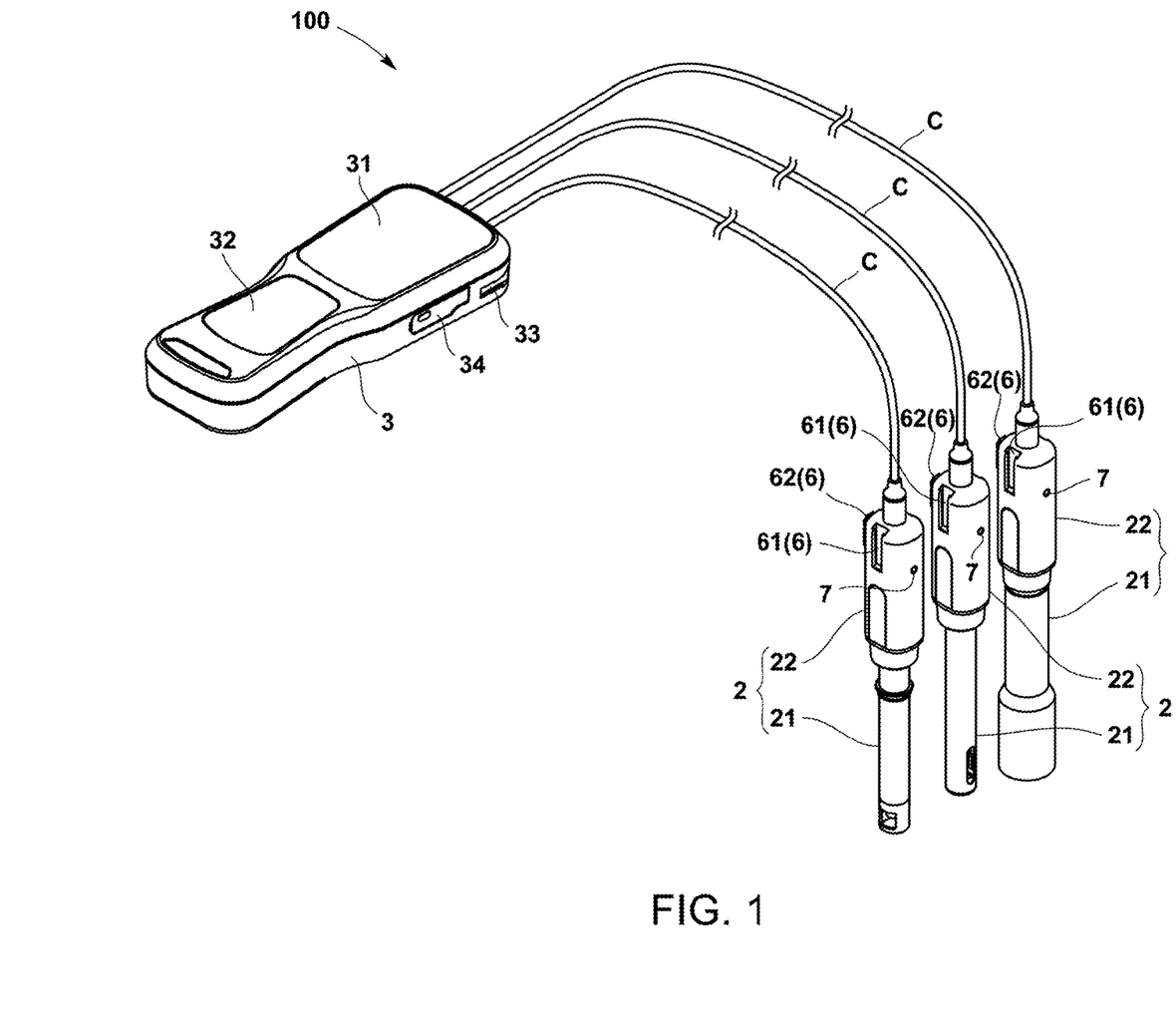
FIG. 1 is an overall schematic view of a liquid analysis device according to an embodiment of the present invention.
Figure 2:
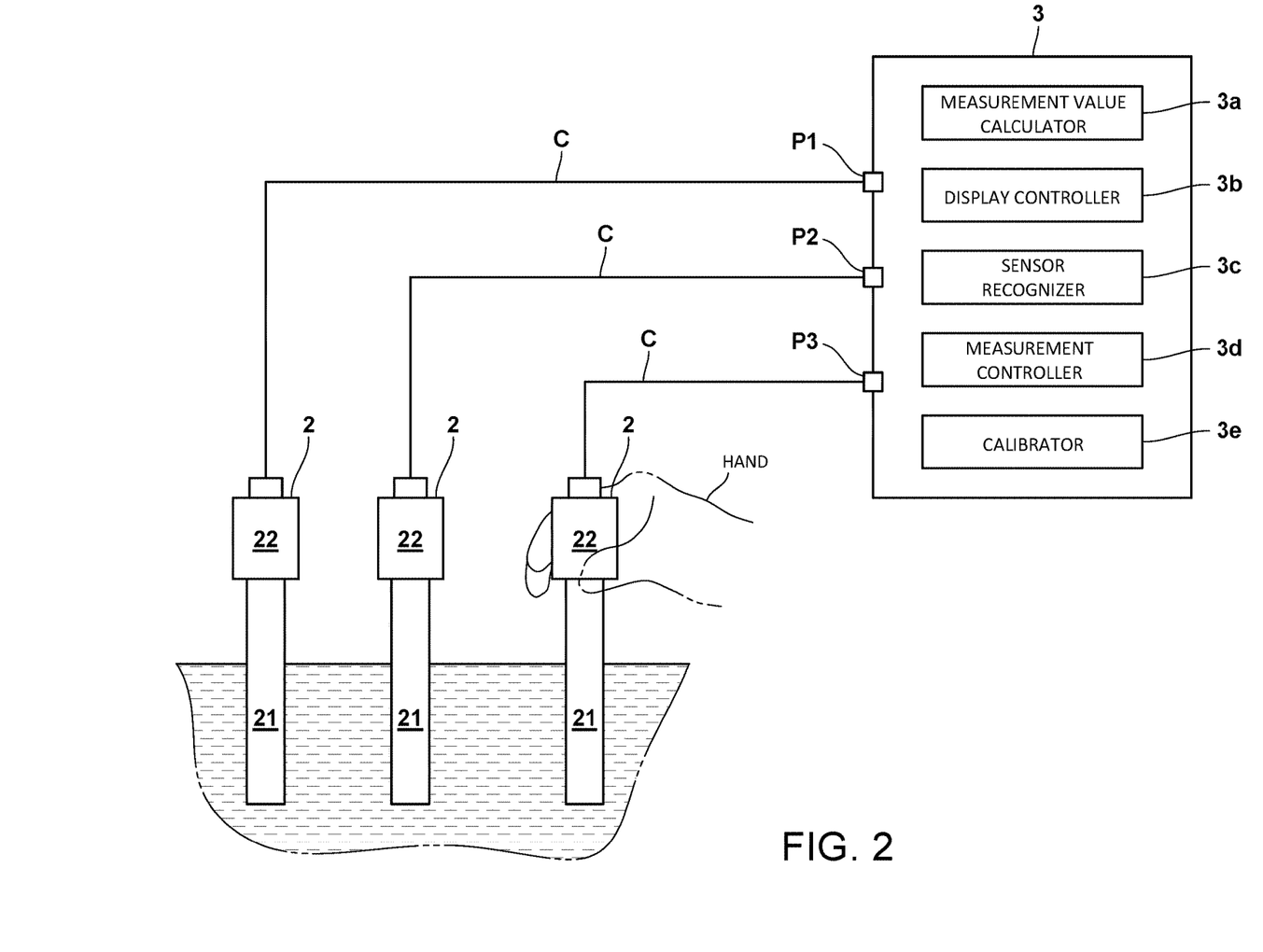
FIG. 2 is a functional block diagram of a device body according to the embodiment.

Specifically, the liquid analysis device 100 is of an immersion type used for field measurement, for example, and includes a sensor unit 2 that is immersed in a liquid and measures a predetermined measurement target item, and a device body 3 to which the sensor unit 2 is connected, as illustrated in FIGS. 1 and 2. In the embodiment, the sensor unit 2 and the device body 3 are connected by a cable C for signal transmission and power supply.

Each component will be described below.

2. Sensor Unit

In the embodiment, a sensor unit 2 for pH measurement, a sensor unit 2 for EC measurement, and a sensor unit 2 for DO measurement are provided.

Figure 3:
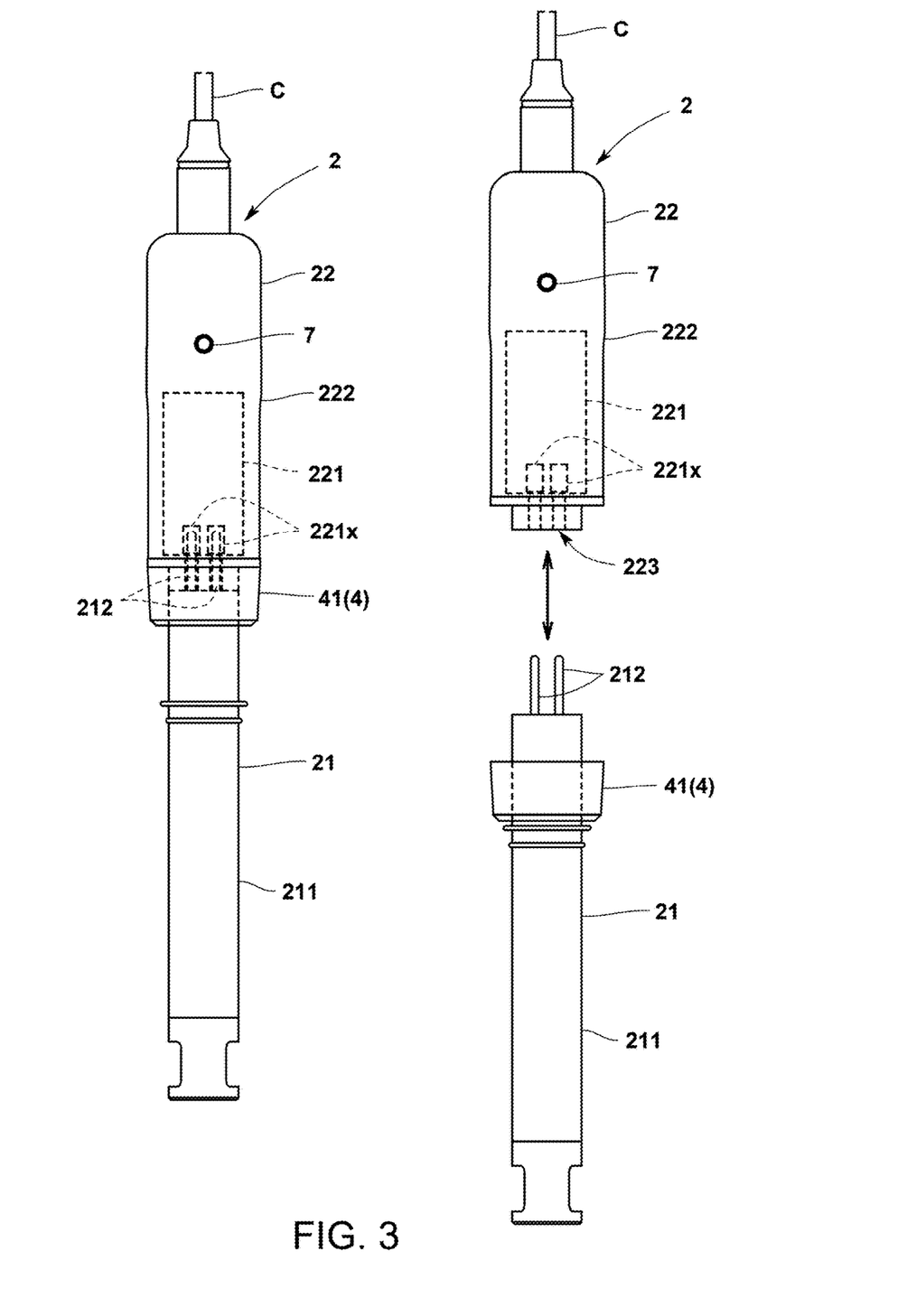
FIG. 3 is a front view of a sensor unit according to the embodiment in an assembled state and the sensor unit in a separated state.

As particularly illustrated in FIG. 3, each of the sensor units 2 includes a sensor portion 21 that contacts a liquid and outputs an analog signal corresponding to a predetermined measurement target item, and a conversion portion 22 that converts the analog signal obtained by the sensor portion 21 into a digital signal. FIG. 3 illustrates the sensor unit 2 for pH measurement. As illustrated in FIG. 2, each sensor unit 2 is used by a user holding the conversion portion 22 in a hand. Specifically, the sensor unit 2 is immersed in the liquid in a state where the user holds the conversion portion 22 in the hand, and thus the sensor portion 21 contacts the liquid.

The sensor portion 21 is provided with a component for measuring a measurement target item in accordance with the measurement target item.

For example, in a case where the sensor portion 21 is a pH sensor that measures pH as a measurement target item, a glass electrode for pH measurement, a comparison electrode, a reference electrode, a temperature compensation electrode, and the like are provided. In a case where the sensor portion 21 is an EC sensor that measures EC as a measurement target item, two electrodes, four electrodes, or the like for EC measurement are provided. In a case where the sensor portion 21 is a DO sensor that measures DO as a measurement target item, a sensitive membrane that emits fluorescence in an amount dependent on an oxygen concentration, a light source that irradiates the sensitive membrane with excitation light that excites fluorescence, and a photodetector that receives the fluorescence emitted from the sensitive membrane are provided. In the sensor portion 21, a component for measuring the measurement target item is held inside a support pipe 211 having a straight pipe shape, for example.

The conversion portion 22 converts an analog signal obtained by the sensor portion 21 into a digital signal. Specifically, the conversion portion 22 includes an amplifier that amplifies the analog signal of the sensor portion 21 and an AD converter that digitally converts the amplified analog signal. The conversion portion 22 is dedicated to each sensor portion. That is, when the sensor portion 21 is a pH sensor, the conversion portion 22 is a pH sensor, when the sensor portion 21 is an EC sensor, the conversion portion 22 is an EC sensor, and when the sensor portion 21 is a DO sensor, the conversion portion 22 is a DO sensor.

Each of the conversion portions 22 is provided with the amplifier and the AD converter on a circuit board 221, and the circuit board 221 is housed in a housing 222 of the conversion portion 22. The cable C electrically connected to the circuit board 221 is connected to an upper end of the housing 222, and the digital signal obtained by the conversion portion 22 is transmitted to the device body 3 via the cable C.

As illustrated in FIG. 3, in the sensor unit 2 according to the embodiment, the sensor portion 21 and the conversion portion 22 are attachable to and detachable from each other.

Figure 4:
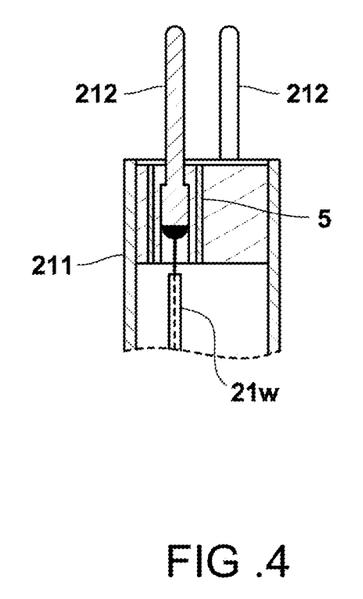
FIG. 4 is a partially enlarged sectional view of a connection plug and a periphery of the connection plug according to the embodiment.

Here, a connection plug 212 for electrically connecting to the conversion portion 22 is provided at an upper end of the support pipe 211 of the sensor portion 21. As illustrated in FIG. 4, the connection plug 212 is electrically connected to a wire 21w of the sensor portion 21 by soldering, for example. An insertion portion 223 into which the connection plug 212 is inserted is formed at a lower end of the housing 222 of the conversion portion 22. By inserting the connection plug 212 of the sensor portion 21 into the insertion portion 223, the connection plug 212 contacts and is electrically connected to a connection terminal 221x provided on the circuit board 221 inside the housing 222.

The sensor portion 21 and the conversion portion 22 are provided with a seal mechanism 4 for liquid-tight sealing while being connected. The seal mechanism 4 includes an O-ring (not illustrated) interposed between the housing 222 of the conversion portion 22 and the support pipe 211 of the sensor portion 21, and a fastening structure 41 for crushing the O-ring with the housing 222 and the support pipe 211. The fastening structure 41 includes, for example, a screw provided on an outer peripheral surface of the housing 222 and a nut provided on the support pipe 211 and screwed to the screw. The seal mechanism 4 secures liquid-tightness of a connection portion between the sensor portion 21 and the conversion portion 22, and strengthens connection between the sensor portion 21 and the conversion portion 22.

Here, in the sensor portion 21, electromagnetic noise is added to the analog signal via a connection portion between the connection plug 212 and the wire 21w of the sensor portion 21. In particular, in a case where the user holds the sensor unit 2 in the hand, the user holds the conversion portion 22 as described above or holds the connection portion between the sensor portion and the conversion portion 22. Then, static electricity from the hand is added to the analog signal as electromagnetic noise. This problem is particularly noticeable when the sensor portion 21 is a pH sensor, and SN of the pH sensor is deteriorated. Therefore, in the embodiment, as shown in FIG. 4, a metal shield 5 is provided at the connection portion between the connection plug 212 and the wire 21w in the pH sensor. The metal shield 5 is, for example, a brass pipe having a cylindrical shape, and is provided so as to surround the connection portion. Note that the sensor portion 21 other than a pH sensor may be provided with the metal shield 5.

3. Device Body

The device body 3 to which the sensor unit 2 configured as described above is connected includes a measurement value calculator 3a that calculates a measurement value of each measurement target item based on the digital signal acquired from the connected sensor unit 2 (see FIG. 2). As illustrated in FIG. 1, on a front surface of the device body 3, the device body 3 has a display 31 that displays a measurement result of the connected sensor unit 2, and an operation button group 32 that controls the connected sensor unit 2 and switches a display of the display. The device body 3 is a computer including a CPU, an internal memory, an input and output interface, and the like. Reference sign 34 in FIG. 1 denotes a cover that protects an output port and a USB port for printing.

Figure 5A:
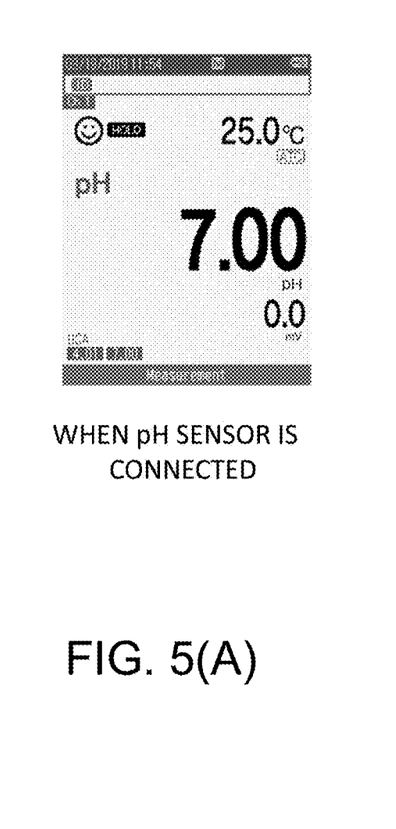
FIGS. 5(A)-5(C) are views illustrating an example of a screen display according to the embodiment.
Figure 5B:
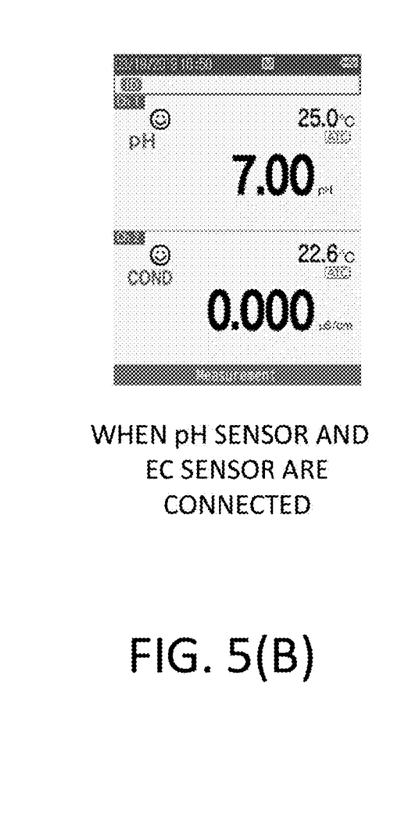
Figure 5C:
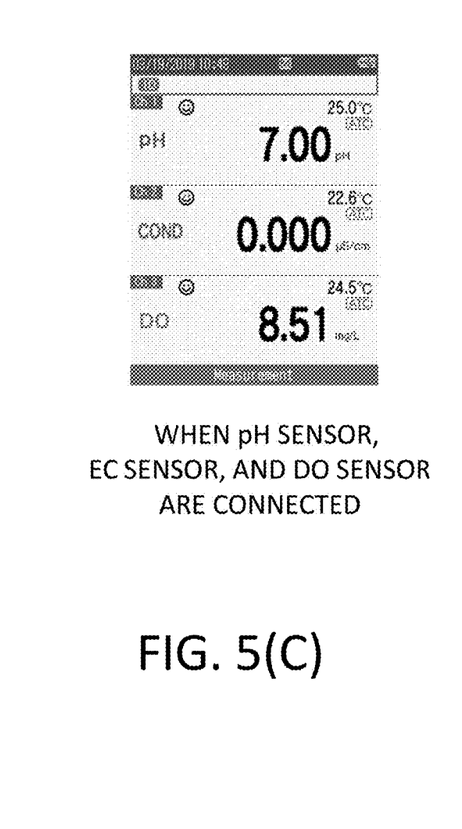

The display 31 displays a measurement result by a display controller 3b of the device body 3. FIGS. 5(A)-5(C) illustrate examples of a screen display by the display controller 3b. FIG. 5(A) illustrates a display screen that displays a measurement result when the pH sensor is connected to the device body 3. FIG. 5(B) illustrates a display screen that displays a measurement result when the pH sensor and the EC sensor are connected to the device body 3. FIG. 5(C) is a display screen that displays a measurement result when the pH sensor, the EC sensor, and the DO sensor are connected to the device body 3. In FIGS. 5(B) and 5(C), when a plurality of sensors are connected, the display screen is divided to display a list of a plurality of measurement target items. However, the display screen can be switched to display each measurement target item, or the number of items to be displayed can be set.

Figure 6:
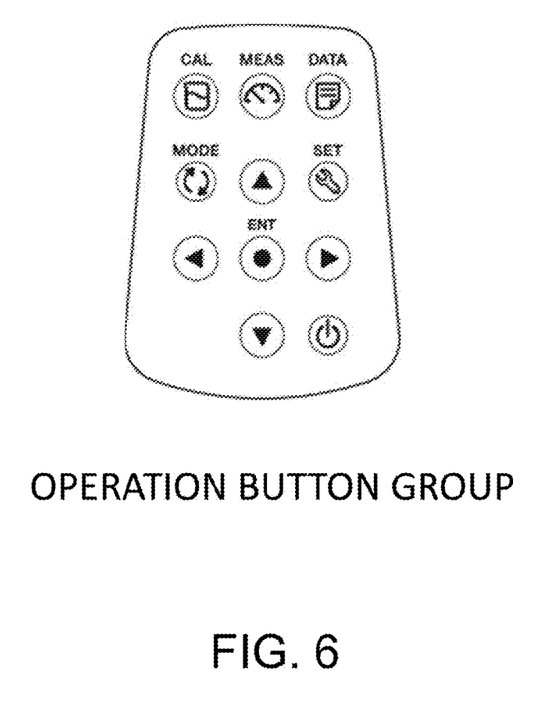
FIG. 6 is a diagram of an operation button group according to the embodiment.

As illustrated in FIG. 6, the operation button group 32 includes a "calibration (CAL) button" for starting calibration, a "measurement (MEAS) button" for starting measurement, a "data (DATA) button" for displaying history data, a "mode (MODE) button" for changing a measurement parameter during measurement, a "setting (SET) button" for setting of display and the like, a "determination (ENT) button" for determining recording of a measurement value during measurement or calibration, a "movement (UP, DOWN, LEFT, and RIGHT) button" for moving up, down, left, and right, and a "power supply (POWER) button" for turning on and off power.

4. Sensor Automatic Recognition

The device body 3 is provided with a plurality of (here, three) connection ports P1 to P3 such that a plurality of sensor units 2 for different measurement target items can be simultaneously connected. These three connection ports P1 to P3 have the same shape, and the three sensor units 2 (conversion portions 22) can be connected equally. That is, any one of the three conversion portions 22 can be connected to the first connection port P1, any one of the three conversion portions 22 can be connected to the second connection port P2, and any one of the three conversion portions 22 can be connected to the third connection port P3. The connection terminals of the cables C connected to the three conversion portions 22 also have the same shape in accordance with the connection ports P1 to P3.

The device body 3 includes a sensor recognizer 3c that recognizes the sensor portion 21 attached to the conversion portion 22 connected to each of the connection ports P1 to P3. Here, the sensor recognizer 3c includes a database including identifiers set for the respective conversion portions 22 and types of sensors associated with the identifiers, acquires the identifiers set for the conversion portions 22 from the conversion portions 22 connected to the connection ports P1 to P3, and recognizes the sensor portions 21 connected to the connection ports P1 to P3 by comparing the identifiers with the database.

5. Coupling Mechanism

Figure 7:
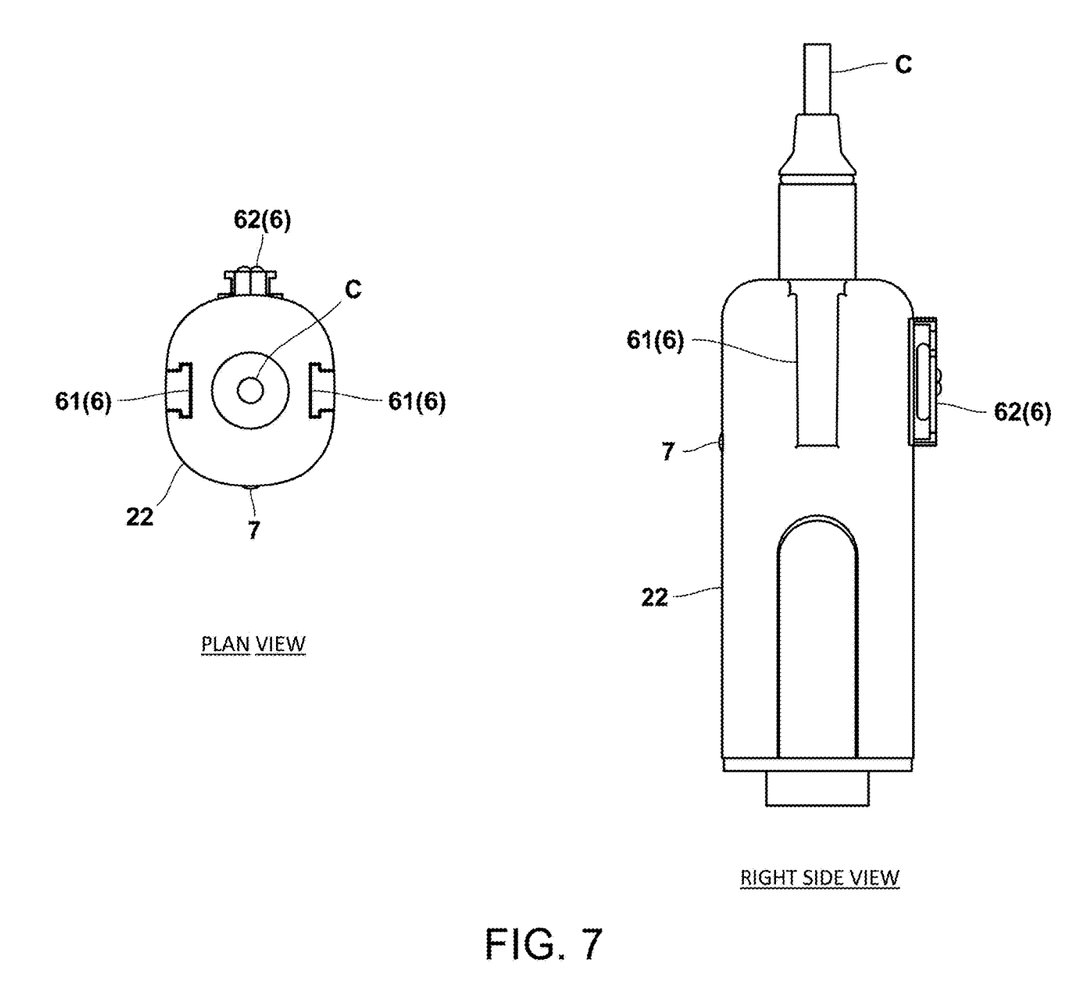
FIG. 7 is a view of a coupling mechanism according to the embodiment.

As illustrated in FIG. 7, the liquid analysis device 100 according to the embodiment includes a coupling mechanism 6 that couples the plurality of conversion portions 22 to each other.

The coupling mechanism 6 couples the plurality of conversion portions 22 such that the sensor portions 21 attached to the conversion portions face in the same direction. Specifically, the coupling mechanism 6 includes a recess 61 formed on a side surface of each conversion portion 22 and a protrusion 62 fitted into the recess 61. Here, the recess 61 is a recessed groove elongated in a vertical direction, and an upper end of the recess 61 is opened. The protrusion 62 is a ridge that slides and fits into the recessed groove. Accordingly, the two conversion portions 22 can be coupled to each other by sliding the protrusion 62 of one of the two conversion portions 22 into the recess 61 of the other conversion portion 22.

Figure 8A:
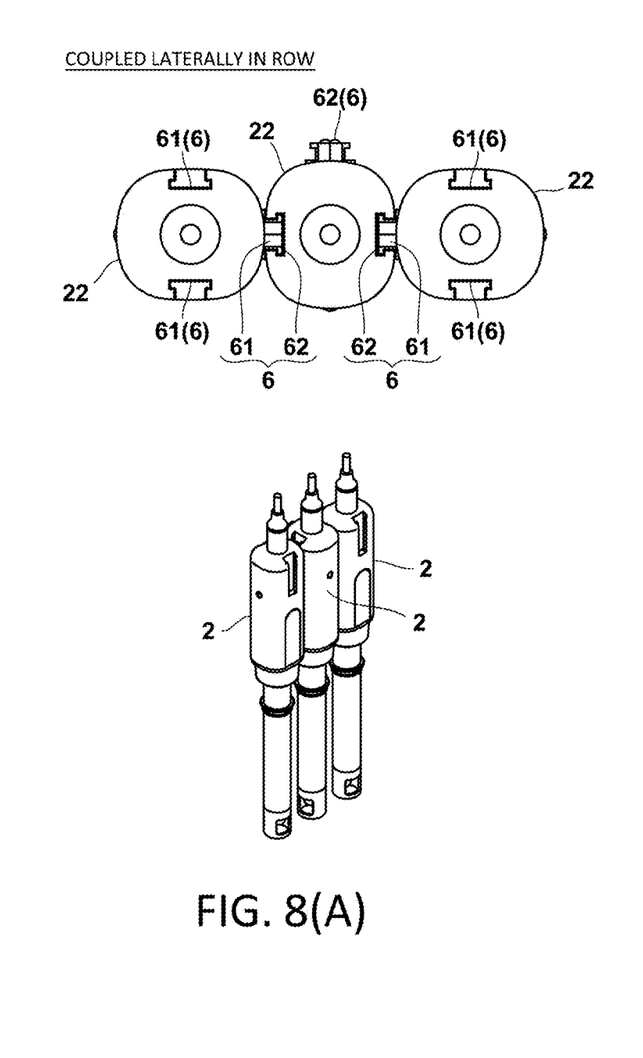
FIGS. 8(A) and 8(B) are views of coupling patterns according to the embodiment.
Figure 8B:
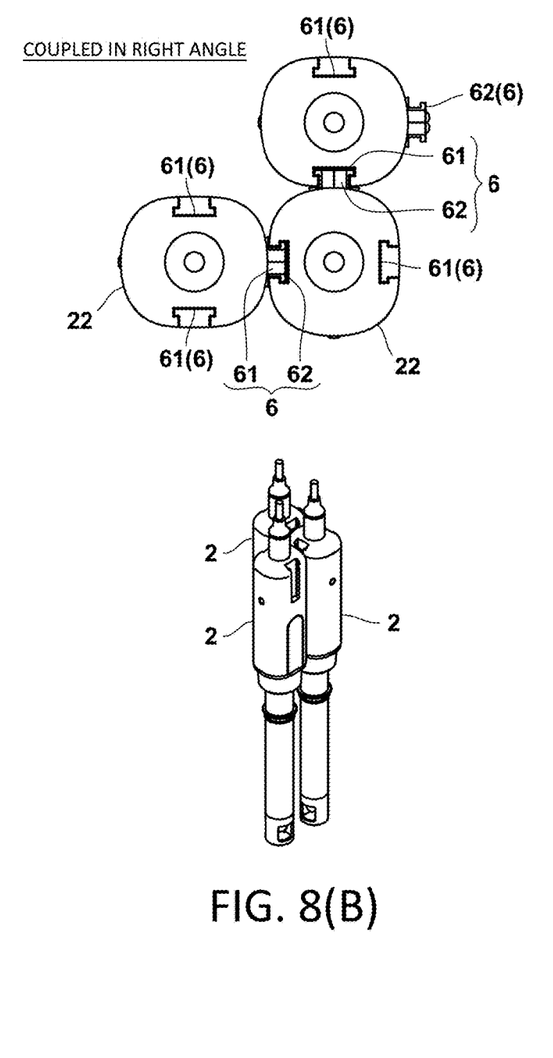

In the embodiment, in each conversion portion 22, one recess 61 is formed on each of the side surfaces (left and right side surfaces) corresponding to each other, and one protrusion 62 is formed on a back surface. Since the recess 61 and the protrusion 62 are formed as described above, the three conversion portions 22 can be laterally coupled in a row (see FIG. 8(A)), or the three conversion portions 22 can be coupled in a right angle (L shape) (see FIG. 8(B)).

In FIG. 7, the conversion portions 22 are coupled by being slid up and down. However, by changing a formation direction of the recess 61 and the protrusion 62, for example, the conversion portions can be slid laterally or obliquely.

The coupling mechanism 6 couples the plurality of conversion portions 22 such that the sensor portions 21 attached to the plurality of conversion portions 22 are located at the same height. That is, the coupling mechanism 6 couples the plurality of conversion portions 22 such that at least one of a position from a bottom of water to a sensing portion or a position from a water surface to the sensing portion in each sensor portion 21 attached to each of the plurality of conversion portions 22 is an identical position. Here, the sensing portion of each sensor portion 21 is a response film of a glass electrode in a pH sensor, an electrode in an EC sensor, and a sensitive film in a DO sensor. In the embodiment, since the conversion portions 22 have the same shape and the sensor portions 21 have the same length, the sensor portions 21 are located at the same height by coupling the plurality of conversion portions 22 by the coupling mechanism 6.

The recess 33 into which the protrusion 62 formed on conversion portion 22 is fitted is formed on a side surface of the device body 3, and the conversion portion 22 can be coupled and fixed to the device body 3 (see FIG. 1).

6. Stability Display Function

Furthermore, in the embodiment, the conversion portion 22 includes the notifier 7 that provides notification that output of the sensor portion 21 is stable during measurement and calibration.

The notifier 7 provides notification by light as to whether the output of the sensor portion 21 is stable. Specifically, the notifier 7 is, for example, a lamp such as an LED exposed to a front surface of the housing 222 of the conversion portion 22. For example, the notifier 7 is controlled to intermittently light up (blink) before the output of the sensor portion 21 (that is, the measurement value by the sensor unit 2) is stable, and to continuously light up when the output of the sensor portion 21 is stable. This lighting control may be performed by a controller (not illustrated) provided on the circuit board of the conversion portion 22, or may be performed by a measurement controller 3d provided in the device body 3.

Regarding this stability display function, the display controller 3b of the device body 3 has a hold function of automatically fixedly displaying the measurement value displayed on the display 31 after the measurement value by the sensor unit 2 is stabilized. This hold function is automatically canceled when a difference between the measurement value at a time of holding and the measurement value after holding is more than or equal to a predetermined value. Alternatively, the user can manually cancel the hold function by pressing the "measurement (MEAS) button" or the like.

The notifier 7, for example, intermittently lights up (blinks) when the conversion portion 22 is connected to the device body 3 via the cable C and power is supplied from the device body 3. Accordingly, the notifier 7 can also determine whether the conversion portion 22 is securely connected to the device body 3. Note that the lighting during the connection may be performed after the sensor recognizer 3c recognizes the sensor portion 21. As a result, it can be seen whether the sensor portion 21 has been recognized after the connection.

7. Simultaneous Calibration Function

Furthermore, the device body 3 according to the embodiment can simultaneously calibrate the plurality of sensor portions 21 for different measurement target items. That is, in the embodiment, three of the pH sensor, the EC sensor, and the DO sensor can be calibrated at the same time.

Figure 9:
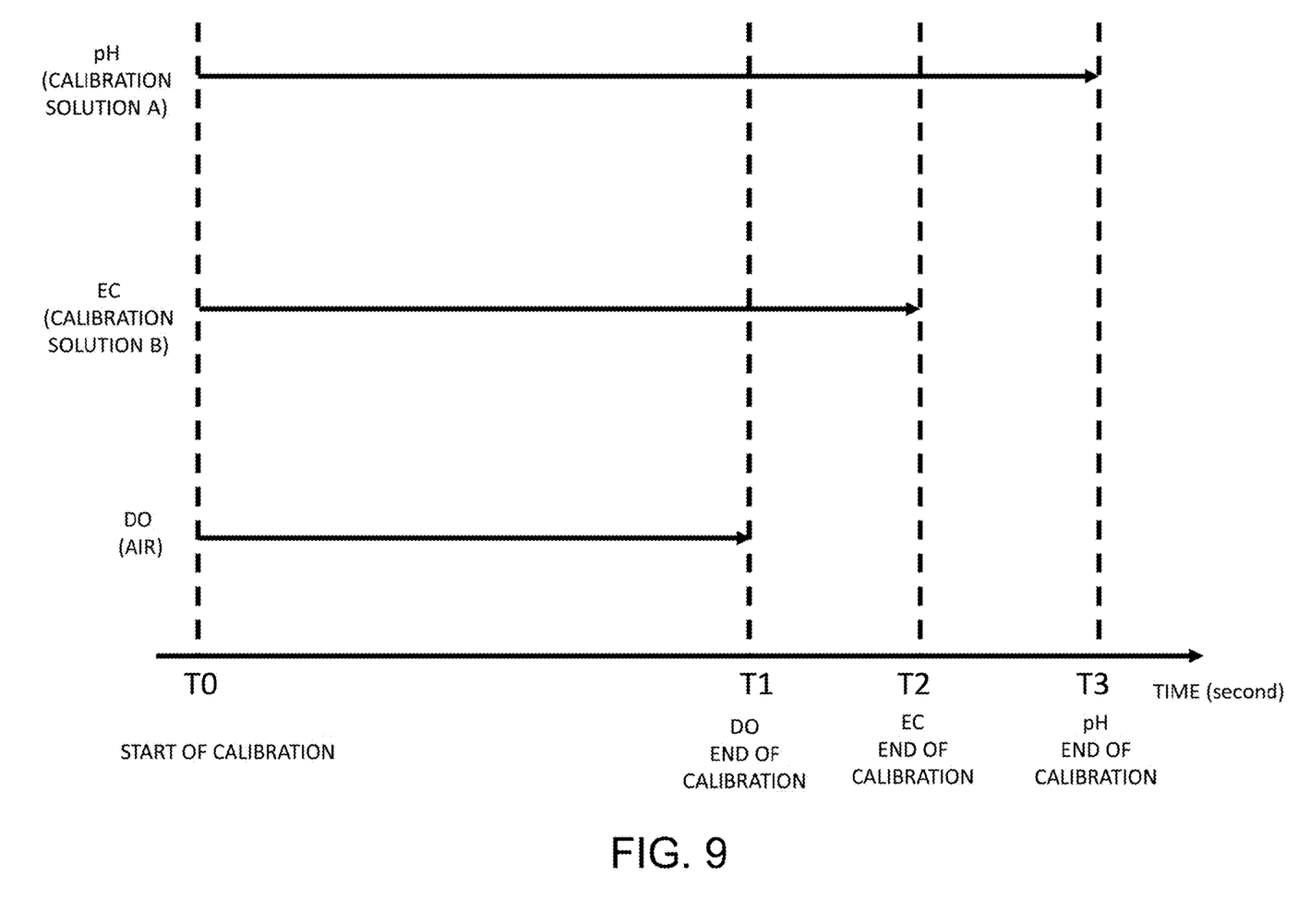
FIG. 9 is a diagram illustrating calibration timing according to the embodiment.

Specifically, the device body 3 includes a calibrator 3e that simultaneously calibrates the plurality of sensor portions 21 for different measurement target items. The pH sensor is immersed in a calibration solution for a pH sensor, the EC sensor is immersed in a calibration solution for an EC sensor, and the DO sensor is exposed to air. In this manner, the sensor portions 21 are calibrated by using different types of calibration substances such as calibration solutions. Then, by pressing an operation button ("calibration (CAL) button") of the device body 3, calibration of each sensor portion 21 is simultaneously started as illustrated in FIG. 9. When calibration is started, an analog signal is output from each sensor portion 21 and is converted into a digital signal by the conversion portion 22. Then, the measurement value calculator 3a of the device body 3 calculates a measurement value indicated by the digital signal. The calibrator 3e calibrates each sensor from the measurement value obtained by the measurement value calculator 3a and the value of each calibration solution. In this manner, calibration processing for each sensor portion 21 after the calibration is started is performed in parallel.

Here, the calibrator 3e can also automatically recognize the calibration solution from the measurement value obtained at a time of calibration. Specifically, the calibrator 3e has a database of calibration solution, specifies the calibration solution used for calibration by comparing the measurement value obtained at the time of calibration with the database, and performs calibration using the specified value of the calibration solution.

8. Stand Member

Figure 10A:
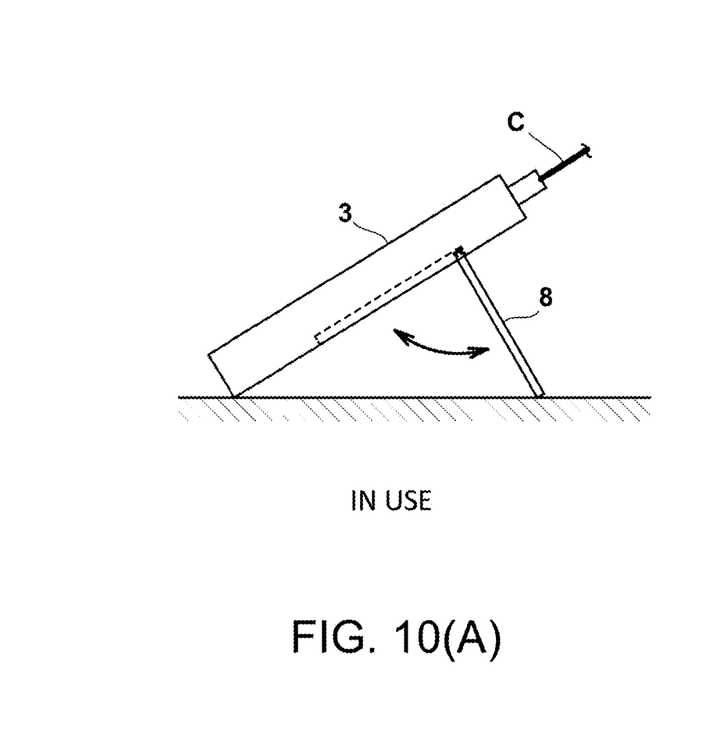
FIGS. 10(A) and 10(B) are schematic views illustrating a state where the device body is placed using a stand member according to the embodiment, and a view illustrating a shape of the stand member.
Figure 10B:
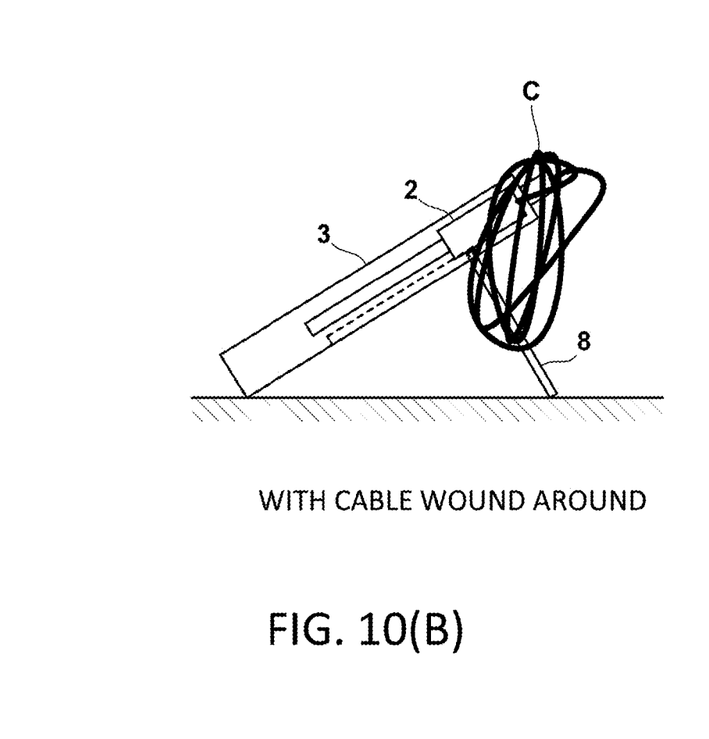

In addition, as illustrated in FIGS. 10(A) and 10(B), the device body 3 according to the embodiment is provided with a stand member 8 that supports the device body 3 in an inclined or standing state. The stand member 8 is storable in a back surface of the device body 3 (a surface opposite to the front surface on which the display 31 is provided). The stand member 8 is rotatably provided between a storage position where the stand member 8 is stored in the back surface of the device body 3 and a support position where the stand member 8 supports the device body 3 in an inclined or standing state.

The cable C is configured to be wound around the stand member 8. Although FIG. 10(B) illustrates an example in which the cable C is wound around the stand member 8 and the device body 3, the cable C may be wound only around the stand member 8. By forming the recess on a side of the stand member 8, the cable C is less bulky in a state of being wound around the stand member 8.

9. Effects of Embodiment

In the liquid analysis device 100 according to the embodiment configured as described above, since the sensor portion 21 and the conversion portion 22 are attachable to and detachable from each other, when the sensor portion 21 is replaced, it is sufficient to replace only the sensor portion 21 and not necessary to replace the conversion portion 22. Thus, a running cost of the liquid analysis device 100 can be reduced. Since the metal shield 5 is provided at the connection portion between the connection plug 212 and the wire 21w of the sensor portion 21, the electromagnetic noise superimposed on the analog signal from the connection portion between the connection plug 212 and the wire 21w of the sensor portion 21 can be reduced, and measurement accuracy can be improved.

10. Other Modified Embodiments

Note that the present invention is not limited to the above embodiment.

For example, in the above embodiment, the device body 3 and the sensor unit 2 are connected by the cable, but the device body 3 and the sensor unit 2 may be wirelessly connected.

Further, the device body 3 may have a voice recognition function. Specifically, the device body 3 may include a voice recognizer, and when the user utters a voice such as "measurement" or "calibration", for example, the device body 3 may recognize the voice and perform measurement or calibration. This voice recognition function is particularly effective in a case where the device body 3 and the sensor unit 2 are located away from each other, and the user cannot simultaneously operate the device body 3 and the sensor unit 2.

Furthermore, in the above embodiment, the device body 3 acquires the digital signal from the sensor unit 2 and calculates the measurement value, but the conversion portion 22 may calculate the measurement value. In this case, a digital signal indicating the measurement value is transmitted to the device body 3.

In the above embodiment, the coupling mechanism 6 couples the plurality of conversion portions 22 such that the sensor portions 21 attached to the conversion portions 22 face in the same direction. In a case where the plurality of conversion portions 22 are coupled by the coupling mechanism 6 in this manner, the user uses the plurality of sensor units 2 by holding the cables C connected to the respective conversion portions 22 in the hand. Specifically, the user immerses the plurality of sensor units 2 in the liquid while holding each cable C in one hand, and thus the sensor portion 21 contacts the liquid. As a result, at least one position in the water of the position from the bottom of water to the sensing portion or the position from the water surface to the sensing portion in the sensor portion 21 is an identical position. Therefore, the liquid analysis device 100 does not require the user to adjust the position of each sensor unit 2 in the water.

In the above embodiment, the liquid analysis device 100 for measuring pH, EC, and DO is exemplified as the measurement target items, but the measurement target items other than pH, EC, and DO can be measured by connecting the sensor unit 2 for measuring other measurement target items to the device body 3.

In addition, various modifications and combinations of the embodiments may be made without departing from the gist of the present invention.

INDUSTRIAL APPLICABILITY

The present invention can reduce the running cost in the liquid analysis device and reduce the electromagnetic noise superimposed on the analog signal.

The invention claimed is:

1. A liquid analysis device comprising:
a plurality of sensor portions each configured to contact a liquid and output an analog signal corresponding to a predetermined measurement target item;
a plurality of conversion portions each configured to convert the analog signal obtained by a respective one of the sensor portions into a digital signal;
a device body to which each conversion portion is connected by a wire or wirelessly, the device body being configured to acquire each digital signal from the respective conversion portion; and
a plurality of coupling mechanisms that couple and fix the conversion portions to each other by bringing a plurality of side surfaces of the conversion portions into contact with each other, wherein
the sensor portions and the conversion portions are attachable to and detachable from each other,
each sensor portion includes a connection plug that electrically connects to the respective conversion portion, and
a metal shield is provided at a connection portion between the connection plug and a wire of at least one of the sensor portions.

2. The liquid analysis device according to claim 1, wherein the sensor portions and the conversion portions are respectively integrated in a state of being electrically connected by the respective connection plug, and are operated by being held in a hand.

3. The liquid analysis device according to claim 2, wherein at least one of the sensor portions to which the metal shield is provided is configured to measure pH as a measurement target item.

4. The liquid analysis device according to claim 1, wherein the conversion portions each include a notifier that provides notification that output of the respective sensor portion is stable during measurement and calibration.

5. The liquid analysis device according to claim 1, wherein the coupling mechanisms couple the conversion portions for at least one of a position from a bottom of water to a respective sensing portion or a position from a water surface to the respective sensing portion in each of the sensor portions attached to each of the conversion portions to be an identical position.

6. The liquid analysis device according to claim 1, wherein
the sensor portions are each for different measurement target items, and
the device body includes a calibrator that simultaneously calibrates the sensor portions for different measurement target items.

7. The liquid analysis device according to claim 6, wherein the device body calibrates the sensor portions for different measurement target items by using different types of calibration substances.

8. The liquid analysis device according to claim 1, wherein the device body includes a plurality of connection ports to which a respective cable extending from each conversion portion is respectively connected, and a sensor recognizer that recognizes the sensor portion attached to the conversion portion connected to each connection port.

9. The liquid analysis device according to claim 1, wherein
the device body is provided with a stand member that supports the device body in an inclined or standing state, and
respective cables connecting the conversion portions and the device body are configured to be wound around the stand member.

10. The liquid analysis device according to claim 1, wherein the coupling mechanisms include:
a recess formed on one of the side surfaces of each conversion portion; and
a protrusion formed on one of the side surfaces of each conversion portion and fitted into the recess.

11. A sensor unit comprising:
a sensor portion configured to contact a liquid and output an analog signal corresponding to a predetermined measurement target item;
a conversion portion configured to convert the analog signal obtained by the sensor portion into a digital signal and output the digital signal to outside; and
a coupling mechanism that couples and fixes the conversion portion to another conversion portion of another sensor unit by bringing a plurality of side surfaces of the conversion portions into contact with each other,
wherein the sensor portion and the conversion portion are attachable to and detachable from each other,
the sensor portion includes a connection plug that electrically connects to the conversion portion, and
a metal shield is provided at a connection portion between the connection plug and a wire of the sensor portion.

* * * * *